United States Patent [19]

Lam et al.

[11] 4,115,582
[45] Sep. 19, 1978

[54] N-1,1,2,2-TETRACHLORO-2-FLUOROETH-YLTHIO BENZANILIDE AND ITS USE AS FUNGICIDE AND ACARICIDE

[75] Inventors: Hsiao-Ling Lam, El Cerrito; Ferenc M. Pallos, Walnut Creek, both of Calif.

[73] Assignee: Stauffer Chemical Company, Westport, Conn.

[21] Appl. No.: 833,525

[22] Filed: Sep. 15, 1977

[51] Int. Cl.$^2$ .................... A01N 9/12; C07C 69/76
[52] U.S. Cl. ...................... 424/298; 260/453 RW
[58] Field of Search ................ 260/453 RW; 424/298

[56] References Cited
FOREIGN PATENT DOCUMENTS
1,317,400  1/1962  France .................... 260/453 RW

*Primary Examiner*—Lewis Gotts
*Assistant Examiner*—Robert C. Whittenbaugh
*Attorney, Agent, or Firm*—Edwin H. Baker

[57] ABSTRACT

N-1,1,2,2-tetrachloro-2-fluoroethylthio benzanilide which has the structural formula

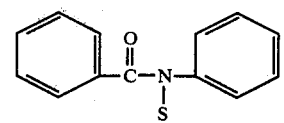

and its use as a fungicide and acaricide.

4 Claims, No Drawings

N-1,1,2,2-TETRACHLORO-2-FLUOROETHYLTHIO BENZANILIDE AND ITS USE AS FUNGICIDE AND ACARICIDE

This invention relates to N-1,1,2,2-tetrachloro-2-fluoroethylthio benzanilide which is useful as a fungicide and acaricide.

The compound of the present invention, N-1,1,2,2-tetrachloro-2-fluoroethylthio benzanilide has the following structural formula

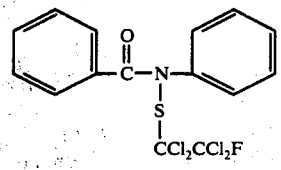

The compound of the present invention can be prepared by the teaching of the following example.

EXAMPLE

N-1,1,2,2-TETRACHLORO-2-FLUOROETHYLTHIO BENZANILIDE

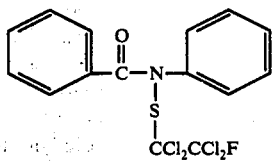

2.36 grams (0.012 mole) benzanilide and 80 milliliters tetrahydrofuran are added to a three necked round bottom reaction flask equipped with a stirrer, reflux condenser and dropping funnel. Next, 0.4 grams, a mole excess, of sodium hydride is added and the mixture stirred at room temperature for one half hour and then refluxed for two hours. Next, 3.03 grams (0.012 mole) of $ClSCCl_2CCl_2F$ dissolved in 50 milliliters tetrahydrofuran is added dropwise over one hour to the reaction mixture which is cooled with an ice bath. After the addition, the reaction mixture is allowed to warm to room temperature and the reaction mixture is stirred overnight.

The solvent is removed from the reaction product by vacuum stripping. The reaction product is then dissolved in methylene chloride. Water is added to destroy any residual sodium hydride. The reaction product is washed three times with water and then dried over $MgSO_4$. The product is vacuum stripped and crystallized from isopropanol to yield 3.2 grams of the desired compound (hereinafter called compound No. 1). m. p. 77°–78° C.

FOLIAR FUNGICIDE EVALUATION TESTS

A. Evaluation for Preventive Action

1. Bean Rust Test

Pinto bean plants (*Phaseolus vulgaris* L.) approximately 10 cm. tall are transplanted into sandy loam soil in three-inch clay pots. The plants are then inverted and dipped for two to three seconds in 50–50 acetone water solution of the test chemical. Test concentrations range from 1000 ppm downward. After the leaves are dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm which will provide 75% or greater reduction in pustule formation as compared to untreated, inoculated plants. These values are recorded in Table I.

2. Bean Powdery Mildew Test

A candidate chemical is prepared and applied in the same manner as for the bean rust test. After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in ppm, which will provide 75% or greater reduction in mycelial formation as compared to untreated, inoculated plants. These values are recorded in Table I.

3. Tomato Early Blight

A candidate compound is dissolved in an appropriate solvent and diluted with a 50–50 acetone water solution. Four week old tomato (*Lycopersicon esculentum*) plants are then sprayed with the solution to the point of runoff. Test concentrations range from 1000 ppm downward. When the leaves are dry, they are inoculated with a water suspension of spores of the early blight fungus (*Alternaria solani* Ellis and Martin) and placed in an environment of 100% humidity for 48 hours. The plants are then removed from the humidity chamber and held until disease lesions appear on the leaves. Effectiveness is recorded as the lowest concentration, in ppm, which will provide 75% or greater reduction in number of lesions formed as compared to untreated, inoculated plants. These values are recorded in Table I.

4. Blue Grass Leaf Spot

A candidate chemical is prepared and applied in the same manner as the tomato early blight test except that four week old Kentucky Bluegrass (*Poa pratensis*) plants are utilized as the host plant. When the leaves are dry, they are inoculated with a water suspension of spores of the blue grass leaf spot fungus (*Helminthosporium sativum*) and placed in an environment of 100% humidity for 48 hours. The plants are then removed from the humidity chamber and held until disease lesions appear on the leaves. Effectiveness is recorded as the lowest concentration, in ppm, which will provide 75% or greater reduction in number of lesions formed as compared to untreated, inoculated plants. These values are recorded in Table I.

B. Evaluation for Eradicant Action

1. Bean Rust Test

Untreated bean plants (*Phaseolus vulgaris* L.) are inoculated with spores of the bean rust fungus (*Uromyces phaseoli* Arthur) and placed in an environment with 100% humidity for 24 hours. The plants are then removed from the humidity chamber and held in the greenhouse for 2 days to allow the disease to become established. A candidate chemical is then prepared and applied in the same manner as in the bean rust test in Evaluation for Preventive Action. Eradicative effectiveness is recorded as the lowest concentration, in ppm, which will provide a 75% or greater reduction in number of pustules appearing on the leaves as compared to untreated inoculated plants. These values are recorded in Table I.

2. Bean Powdery Mildew Test

Untreated pinto bean plants are dusted with spores of the powdery mildew fungus (*Erysiphe polygoni* De Canolle) and maintained in the greenhouse until mycelial growth appears in the leaf surface. A candidate chemical is then prepared and applied in the same manner as for the bean rust test. Four days later the leaves are examined for inhibition of further mycelial growth. Eradicative effectiveness is recorded as the lowest concentration, in ppm, which will provide a 75% or greater inhibition of viable, sporulating mycelium as compared to untreated inoculated plants. These values are recorded in Table I.

TABLE I

| | | Preventive Action | | |
|---|---|---|---|---|
| Compound Number | Bean Rust | Bean Powdery Mildew | Tomato Early Blight | Blue Grass Leaf Spot |
| 1 | 5 | 10 | 500 | 10 |

| | Fradicant Action | |
|---|---|---|
| Compound Number | Bean Rust | Bean Powdery Mildew |
| 1 | * | 50 |

*No control at 1000 ppm and not tested at higher concentrations

ACARICIDAL EVALUATION TEST

The two-spotted mite (2SM), *Tetranychus urticae* (Koch), is employed in tests for miticides. The test procedure is as follows:

Pinto bean plants (*Phaseolus sp.*) approximately 10 cm. tall, are transplanted into sandy loam soil in 3-inch clay pots and thoroughly infested with two-spotted mites of mixed ages and sexes. Twenty-four hours later, the infested plants are inverted and dipped for two-three seconds in 50-50 acetone-water solution of the test chemical. Treated plants are held in the greenhouse, and 7 days later mortality is determined for both the adult mites and the nymphs hatching from eggs which were on the plants at the time of treatment. Test concentrations range from 0.05% down to that at which 50% mortality occurs. $LD_{50}$ values are expressed below in Table II under the headings "2SM-PE" (i.e., post-embryonic) and "2SM-Eggs", in terms of percent concentration of the test compound in the solution.

TABLE II

| Compound Number | 2SM-PE (%) | 2SM-Eggs (%) |
|---|---|---|
| 1 | .003 | .01 |

The compound of this invention is generally embodied into a form suitable for convenient application. For example, the compound can be embodied into a pesticidal composition which is provided in the form of emulsions, suspensions, solutions, dusts and aerosol sprays. In general, such compositions will contain, in addition to the active compound, the adjuvants which are found normally in pesticide preparations. In these compositions, the active compound of this invention can be employed as the sole pesticide component or it can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pryophyllite; diatomite; gypsum; clays, propellants, such as dichlorodifluoromethane, etc. If desired, however, the active compound can be applied directly to feedstuffs, seeds, etc., upon which the pests feed. When applied in such a manner, it will be advantageous to use a compound which is not volatile. In connection with the activity of the presently disclosed pesticidal compound, it should be fully understood that it is not necessary that they be active as such. The purpose of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

I claim:
1. N-1,1,2,2-tetrachloro-2-fluoroethylthio benzanilide.
2. A composition of matter comprising N-1,1,2,2-tetrachloro-2-fluoroethylthio benzanilide and an inert carrier.
3. A method of controlling fungi comprising applying thereto a fungicidally effective amount of N-1,1,2,2-tetrachloro-2-fluoroethylthio benzanilide.
4. A method of controlling acarids comprising applying thereto an acaricidally effective amount of N-1,1,2,2-tetrachloro-2-fluoroethylthio benzanilide.

* * * * *